US011147795B2

(12) United States Patent
Njardarson et al.

(10) Patent No.: US 11,147,795 B2

(45) Date of Patent: Oct. 19, 2021

(54) NEUROPROTECTIVE COMPOUNDS AND METHODS OF USE

(71) Applicant: ARIZONA BOARD OF REGENTS ON BEHALF OF THE UNIVERSITY OF ARIZONA, Tucson, AZ (US)

(72) Inventors: Jon T. Njardarson, Tucson, AZ (US); Isaac Chogii, Tucson, AZ (US); David Townsend Smith, Tucson, AZ (US); Edon Vitaku, Tucson, AZ (US); Daniela C. Zarnescu, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/515,743

(22) Filed: Jul. 18, 2019

(65) Prior Publication Data

US 2019/0350902 A1 Nov. 21, 2019

Related U.S. Application Data

(63) Continuation-in-part of application No. 15/329,615, filed as application No. PCT/US2015/041169 on Jul. 20, 2015, now Pat. No. 10,358,438.

(60) Provisional application No. 62/714,256, filed on Aug. 3, 2018, provisional application No. 62/027,209, filed on Jul. 21, 2014, provisional application No. 62/038,143, filed on Aug. 15, 2014, provisional application No. 62/131,948, filed on Mar. 12, 2015.

(51) Int. Cl.

| | |
|---|---|
| ***A61K 31/404*** | (2006.01) |
| ***A61K 31/4025*** | (2006.01) |
| ***A61K 31/437*** | (2006.01) |
| ***A61P 25/28*** | (2006.01) |
| *A61K 45/06* | (2006.01) |

(52) U.S. Cl.

CPC ........ *A61K 31/404* (2013.01); *A61K 31/4025* (2013.01); *A61K 31/437* (2013.01); *A61P 25/28* (2018.01); *A61K 45/06* (2013.01)

(58) Field of Classification Search

None

See application file for complete search history.

(56) References Cited

PUBLICATIONS

Schafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Fang et al., Small molecule modulation of TDP-43 recruitment to stress granules prevent persistent TDP-43 accumulation in ALS/FTD. Neuron, 2019, 103, p. 802-819.*

Grant& Hackh's Chemical Dictionary (5th Ed. 1987) at p. 148.*

Alimi et al., Photochemical C-H Activation: Generation of Indole and Carbazole Libraries, and First Total Synthesis of Clausenawalline D. European Journal of Organic Chemistry, 2017, 3197-3210.*

* cited by examiner

*Primary Examiner* — Po-Chih Chen

(74) *Attorney, Agent, or Firm* — Don D. Cha; HDC Intellectual Property Law, LLP

(57) ABSTRACT

The present invention provides compounds and methods for mitigating a clinical condition associated with a neurodegenerative disease or a locomotor dysfunction in a subject. In one particular aspect, the invention relates to compounds and methods for reducing TDP-43 aggregation or toxicity in a subject. The compounds of the invention include those having the following formulas:

I

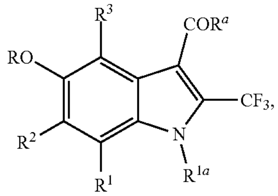

or

II

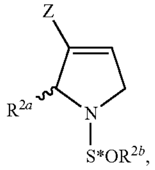

or a pharmaceutically acceptable salt thereof wherein denotes a chiral center;

each of R and $R^{3a}$ is independently hydrogen or alkyl;

$R^a$ is $-CF_3$, $-OR^{a1}$, or $-NR^{b1}R^{b2}$;

$R^{a1}$ is H or alkyl;

each of $R^{b1}$ and $R^{b2}$ is independently H or alkyl;

X is $-NR^{1a}-$, wherein $R^{1a}$ is hydrogen, alkyl or a nitrogen protecting group;

each of $R^1$, $R^2$ and $R^3$ is independently hydrogen, alkyl, haloalkyl, halide, vinyl, alkynyl, —CHO, $-C(=O)R^{1b}$ (ketone), $-CO_2R^{1c}$ (ester), $-OR^{1d}$, $OSO_2R^{1e}$, aryl and heteroaryl, wherein each of $R^{1b}$, $R^{1c}$, $R^{1d}$ and $R^{1e}$ is independently alkyl or aryl;

$R^{2a}$ is hydrogen, alkyl, haloalkyl, aryl, aralkyl, alkenyl, aralkenyl, cycloalkyl, heteroalkyl, heteroaryl or ester functional group;

$R^{2b}$ is alkyl, cycloalkyl, aralkyl, alkenyl, aralkenyl, heteroalkyl, or heteroaryl; and Z is a conjugated electron withdrawing group.

12 Claims, 2 Drawing Sheets

NEUROPROTECTIVE COMPOUNDS AND METHODS OF USE

CROSS-REFERENCE TO RELATED APPLICATIONS

This application is a continuation-in-part of U.S. patent application Ser. No. 15/329,615, filed Jan. 27, 2017, which is a U.S. National Stage Patent Application of PCT Patent Application No. PCT/US15/41169, filed Jul. 20, 2015, which claims the priority benefit of U.S. Provisional Application Nos. 62/027,209, filed Jul. 21, 2014; 62/038,143, filed Aug. 15, 2014; and 62/131,948, filed Mar. 12, 2015. This application also claims the priority benefit of U.S. Provisional Application No. 62/714,256, filed Aug. 3, 2018. All of these applications are incorporated herein by reference in their entirety.

STATEMENT REGARDING FEDERALLY FUNDED RESEARCH

This invention was made with government support under Grant No. CHE1266365 awarded by NSF. The government has certain rights in the invention.

FIELD OF THE INVENTION

The present invention provides compounds and methods for mitigating a clinical condition associated with a neurodegenerative disease or a locomotor dysfunction in a subject. In one particular aspect, the invention relates to compounds and methods for reducing TDP-43 aggregation or toxicity in a subject. The compounds of the invention include those having the following formulas:

I

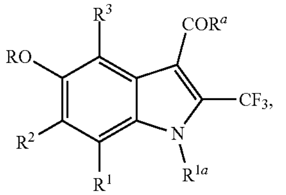

or

II

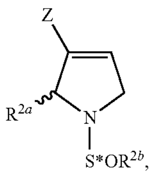

or a pharmaceutically acceptable salt thereof.
wherein *, R, $R^{3a}$, $R^a$, X, $R^1$, $R^2$, and $R^3$, $R^{2a}$, $R^{2b}$, and Z are those defined herein.

BACKGROUND OF THE INVENTION

Amyotrophic Lateral Sclerosis (ALS) is an adult onset, progressive neurological disorder characterized by selective degeneration and death of motor neurons in the motor cortex and the spinal cord. Approximately 10% of all ALS cases are inherited and have been linked to a number of genes including superoxide dismutase (SOD1) and more recently C9ORF72 among others. However, 90% of the known ALS cases are sporadic and remain poorly understood. The ALS pathology includes ubiquitin positive cytoplasmic bodies, which have been shown to contain a 28 kDa fragment corresponding to the C-terminus domain of TDP-43 protein together with the full length TDP-43. TDP-43 is a transactive response (TAR) DNA binding protein with Mw 43 kDa (TDP-43) and represents the major pathological marker, in both ALS and frontotemporal degeneration (FTD), in particular the most common pathological subtype of FTD, i.e., frontotemporal lobar degeneration with ubiquitinated inclusions, FTLD-U. Several missense mutations have been identified in TDP-43, the majority of which lie within the C-terminal region, indicating that this domain may be involved in the pathogenesis of ALS. Notably, TDP-43 pathology is associated with 97% of ALS (familial and sporadic) and 45% of frontotemporal dementia (FTD) cases.

Despite advances in understanding the physiology and pathophysiology of ALS and FTD, there is still a need for compounds that are potent, efficacious, and safe in the treatment or amelioration of ALS as well as other clinical conditions associated with a neurodegenerative disease or locomotor dysfunction or present TDP-43 pathology.

SUMMARY OF THE INVENTION

Some aspects of the invention are based at least in part on understanding of pathways related to ALS and FTD. In particular, some embodiments of the invention are based in part on understanding that TDP-43 has been identified as one of the major pathological proteins in both ALS and the most common pathological subtype of FTD. In addition, TDP-43 pathology in form of cellular aggregates has been recently identified in Alzheimer's Disease, Parkinson's Disease, as well as in traumatic brain injury. Some aspects of the invention are based on the present inventors understanding of insights into the pathogenesis of these conditions and the development of new diagnostic tests and therapies.

One particular aspect of the invention provides a method for mitigating, ameliorating, or preventing locomotor dysfunction in a subject in need thereof. The method includes the step of administering to the subject a therapeutically effective amount of at least one compound having the following chemical formula:

I

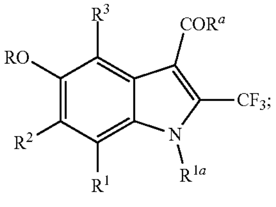

II

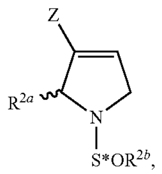

or a pharmaceutically acceptable salt thereof, or a combination thereof, thereby treating the clinical condition associated with locomotor dysfunction in said subject,
where * denotes a chiral center; each of R and $R^{3a}$ is independently hydrogen or alkyl; $R^a$ is —$CF_3$, —$OR^{a1}$, or —$NR^{b1}R^{b2}$, $R^{a1}$ is H or alkyl; each of $R^{b1}$ and $R^{b2}$ is independently H or alkyl; $R^{1a}$ is hydrogen, alkyl, or a nitrogen protecting group; each of $R^1$, $R^2$ and $R^3$ is independently hydrogen, alkyl, haloalkyl, halide, vinyl, alkynyl, —CHO, —C(═O)$R^{1b}$ (ketone), —$CO_2R^{1c}$ (ester), —$OR^{1d}$, $OSO_2R^{1e}$, aryl and heteroaryl, wherein each of $R^{1b}$, $R^{1c}$, $R^{1d}$ and $R^{1e}$ is independently alkyl or aryl; $R^{2a}$ is hydrogen, alkyl, haloalkyl, aryl, aralkyl, alkenyl, aralkenyl, cycloalkyl, heteroalkyl, heteroaryl or ester functional group; $R^{2b}$ is alkyl, cycloalkyl, aralkyl, alkenyl, aralkenyl, heteroalkyl, or heteroaryl; and Z is a conjugated electron withdrawing group.

Another aspect of the invention provides a method for treating a clinical condition associated with a neurodegenerative disease or locomotor dysfunction in a subject, said method comprising administering to the subject in need of such a treatment a therapeutically effective amount of a compound of the formula I or II or a pharmaceutically acceptable salt thereof, or a combination thereof, thereby treating the clinical condition associated with locomotor dysfunction in said subject.

Yet another aspect of the invention provides a method for reducing TDP-43 toxicity or aggregation in a subject, said method comprising the step of administering to the subject a therapeutically effective amount of at least one compound selected from the group consisting of a compound of the formula I or II or a pharmaceutically acceptable salt thereof, or a combination thereof, thereby reducing TDP-43 toxicity or aggregation in said subject.

In some embodiments, administration of a compound of the formula I or II or a pharmaceutically acceptable salt thereof, or a combination thereof does not affect TDP-43 expression. In particular, when the compound of the invention is administered, the expression level of TDP-43 is within 10%, typically within 5%, and often within 2%, and most often within the experimental error range of TDP-43 expression level as that of pre-administration of the compound.

Yet in other embodiments, the neurodegenerative disease is selected from the group consisting of Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, transient ischemic attack, encephalopathy, traumatic brain injury (TBI), and any combination thereof.

Still in other embodiments, the clinical condition comprises Amyotrophic Lateral Sclerosis (ALS), frontotemporal degeneration (FTD), Alzheimer's Disease, encephalopathy, or traumatic brain injury (TBI). In some instances, the FTD comprises frontotemporal lobar degeneration with ubiquitinated inclusions (FTLD-U). In other instances, the treatment comprises ameliorating a symptom associated with ALS.

In other embodiments, the treatment comprises preventing the neurodegenerative disease in the subject.

Yet still in other embodiments, the method also includes administering another or a second compound that relieves a symptom associated with ALS. Such a second compound includes those compounds that are known to one skilled in the art to be effective in treating ALS such as (i) those that are approved by the Food and Drug Administration (FDA) at the filing date of this application; (ii) those that are undergoing clinical trials for treatment of ALS as of the filing date of this application; as well as (iii) those that are developed after the filing date of this application. Specific examples of the second compound include, but are not limited to, riluzole and Radicava.

Still in another embodiment, the method further includes administering to said subject a compound comprising baclofen, trihexyphenidyl hydrochloride, morphine sulfate, lorazepam, glycopyrrolate, benztropine mesylate, gabapentin, Valium® (diazepam), tizanidine, phenytoin sodium, Elavil® (amitriptyline hydrochloride), Cogentin® (benztropine mesylate), ReQuip®, Robinul® (glycopyrrolate), Cuvposa® (glycopyrrolate), Atropine sulphate, Luvox® (fluvoxamine maleate), Dantrium® (dantrolene sodium), Dilantin® (phenytoin sodium), Neurontin® (gabapentin), morphine sulfate, dexpramipexole, or a combination of two or more thereof.

In one particular embodiment, the compound of formula I and II is selected from the group consisting of:

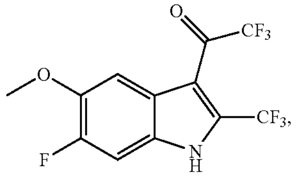

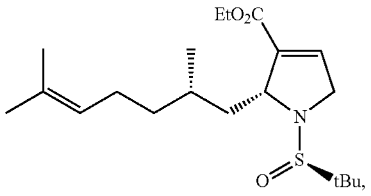

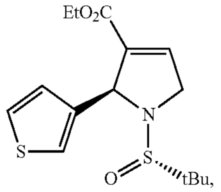

and a combination thereof.

Yet another aspect of the invention provides a composition comprising a compound of the formula I and/or II.

In some embodiments, $R^{1a}$, $R^1$, and $R^3$ are H, $R^2$ is halide, and R is alkyl.

Still in other embodiments, * is an (R)- or (S)-configuration and $R^{2b}$ is alkyl, Z is an ester, and $R^{2a}$ is alkenyl or heteroaryl.

Yet in other embodiments, a diastereomeric excess of compound of formula II is at least 90% d.e. In one particular embodiment, the compound of formula II is selected from the group consisting of:

(i)

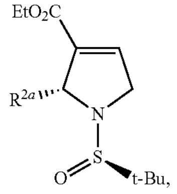

where $R^{2a}$ is alkenyl; and (ii)

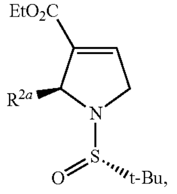

where $R^{2a}$ is heteroaryl.

In one particular embodiment of the invention, the composition includes a compound selected from the group consisting of:

EV-3-298

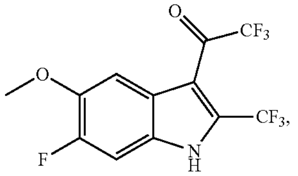

CH-I-108

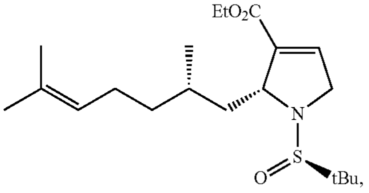

CH-III-31

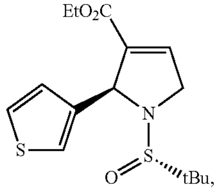

a pharmaceutically acceptable salt thereof, and a combination thereof.

Disclosed herein are compositions comprising a compound having the chemical structure:

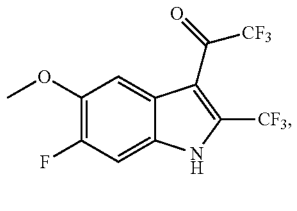

-continued

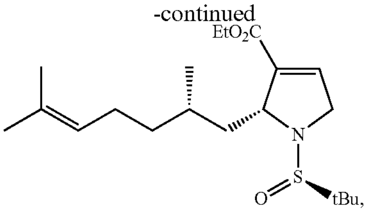

or

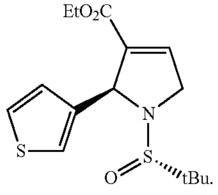

DETAILED DESCRIPTION OF THE INVENTION

Figure 1:
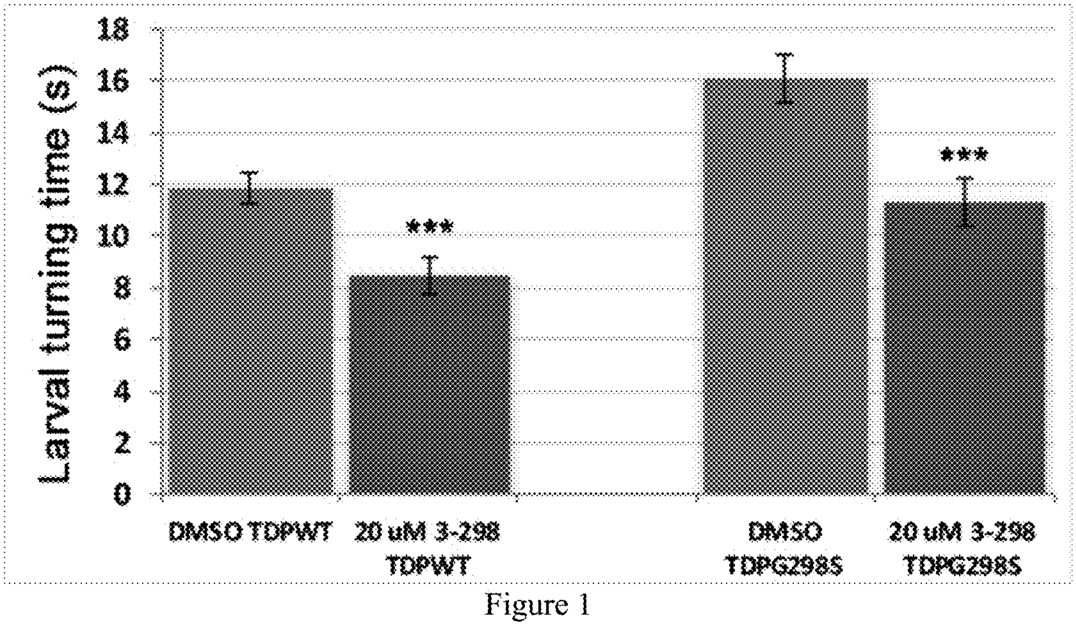
FIG. 1 shows compound EV-3-298 improves locomotor function in larvae expressing either TDPWT of TDPG298S in motor neurons. Student's t-test was used to evaluate statistical significance (***=$P_{value}$<0.001; N>20 larvae/genotype).

Definitions: Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

When referring to a numerical value, the terms "about" and "approximately" are used interchangeably herein and refer to being within an acceptable error range for the particular value as determined by one of ordinary skill in the art, which will depend in part on how the value is measured or determined, e.g., the limitations of the measurement system, i.e., the degree of precision required for a particular purpose. In some embodiments, the term "about" typically means within 1 standard deviation, per the practice in the art. Alternatively, the term "about" can mean ±20%, typically ±10%, often ±5% and more often ±1% of the numerical value. In general, however, where particular values are described herein, unless otherwise stated, the term "about" means within an acceptable error range for the particular value.

As used herein, the terms "optional" or "optionally" means that the subsequently described event or circumstance can or cannot occur, and that the description includes instances where said event or circumstance occurs and instances where it does not.

As used herein, the term "subject" refers to the target of administration, e.g., an animal. In an aspect, the subject of the herein disclosed methods can be a *Drosophila*. In an aspect, the subject of the herein disclosed methods can be mammal, a fish, a bird, a reptile, or an amphibian. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. In an aspect, the subject is a mammal. A patient refers to a subject afflicted with a disease or disorder. The term "patient" includes human and veterinary subjects. In some aspects of the disclosed methods, the subject has been diagnosed with a need for treatment for amyotrophic lateral sclerosis, such as, for example, prior to the administering step.

As used herein, the term "treatment" refers to the medical management of a subject or a patient with the intent to cure, ameliorate, stabilize, mitigate, or prevent a disease, pathological condition, or disorder, such as, for example, ALS or FTD. This term includes active treatment, that is, treatment directed specifically toward the improvement, mitigation, and/or amelioration of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder (such as ALS or FTD). In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving, ameliorating, or mitigating the disease, e.g., causing regression or further advancement of the disease. In an aspect, the disease, pathological condition, or disorder is amyotrophic lateral sclerosis.

As used herein, the term "prevent" or "preventing" refers to precluding, averting, obviating, forestalling, stopping, or hindering something from happening, especially by advance action. In an aspect, prevent or preventing refers to the ameliorating of one or more signs and symptoms associated with ALS or FTD. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by compositions or methods disclosed herein. For example, "diagnosed with amyotrophic lateral sclerosis" means having been subjected to a physical examination by a person of skill, for example, a physician, and found to have a condition that can be diagnosed or treated by a compound or composition that alleviates or ameliorates one or more symptoms associated with amyotrophic lateral sclerosis.

Some aspects of the invention provides a method for diagnosing for the presence of TDP-43 in a sample such that the expression level or expression pattern of TDP-43 indicates to a clinician that the sample is indicative of a clinical condition associated with a neurodegenerative disease or a locomotor dysfunction. Diagnosing can further include comparing the level or binding pattern of TDP-43 to a reference sample that indicates that the subject (or sample) suffers from (contains) a TDP-43 proteinopathy. TDP-43 aggregates are associated with TDP-43 proteinopathy. Diagnosing can also include identifying mutations (e.g., mutations in SOD1 or FUS) by sequencing that indicates to a clinician that the sample is indicative of a clinical condition associated with a neurodegenerative disease or a locomotor dysfunction such as ALS.

Some embodiments of such methods comprise determining the expression level of TDP-43 in a sample obtained from the subject. As used herein, the term "expression" refers to (1) detecting transcription and/or translation of TDP-43 gene, (2) detecting or determining the amount of TDP-43 present in the sample, or (3) both. To detect expression of a gene refers to the act of actively determining whether a gene is expressed or not. This can include determining whether the gene expression is upregulated as compared to a control, downregulated as compared to a control, or substantially unchanged as compared to a control. Therefore, the step of detecting expression does not require that expression of the gene actually is upregulated or downregulated, but rather, can also include detecting no expression of the gene or detecting that the expression of the gene has not changed or is not different (i.e., detecting no significant expression of the gene or no significant change in expression of the gene as compared to a control).

According to the invention, a "control" can include a normal or negative control and/or a disease or positive control, against which a test level of TDP-43 expression can be compared. Therefore, it can be determined, based on the control expression level of TDP-43, whether a sample to be evaluated for a clinical condition associated with a neurodegenerative disease or a locomotor dysfunction has a measurable difference or substantially no difference in the TDP-43 expression level, as compared to the control level. In one aspect, the control is an indicative of the expression level of TDP-43 as expected in a normal (e.g., healthy, negative control) patient.

As used herein, the phrase "identified to be in need of treatment for a disorder," or the like, refers to selection of a subject based upon need for treatment of the disorder. For example, a subject can be identified as having a need for treatment of a neurodegenerative disorder (e.g., amyotrophic lateral sclerosis) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. In an aspect, administering can refer to oral administration, such as, in food. Administration can be continuous or intermittent. In various aspects, a preparation can be administered therapeutically; that is, administered to treat an existing disease or condition. In further various aspects, a preparation can be administered prophylactically; that is, administered for prevention of a disease or condition, such as, for example, amyotrophic lateral sclerosis.

The term "contacting" as used herein in reference to a treatment refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or transcript or polypeptide. For example, determining the amount of a disclosed transcript or polypeptide in a sample as used herein can refer to the steps that the skilled person would take to measure or ascertain some quantifiable value of the transcript or polypeptide (e.g., TDP-43) in the sample. The art is familiar with the ways to measure an amount of the disclosed nucleic acids, transcripts, polypeptides, etc.

The term "level" refers to the amount of a target molecule in a sample, e.g., a sample from a subject. The amount of the molecule can be determined by any method known in the art and will depend in part on the nature of the molecule (i.e., gene, mRNA, cDNA, protein, enzyme, etc.). The art is familiar with quantification methods for nucleotides (e.g., genes, cDNA, mRNA, etc.) as well as proteins, polypeptides, enzymes, etc. It is understood that the amount or level of a molecule in a sample need not be determined in absolute terms, but can be determined in relative terms (e.g., when compares to a control (i.e., a non-affected or healthy subject or a sample from a non-affected or healthy subject) or a sham or an untreated sample).

The terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

The term "pharmaceutically acceptable" describes a material that is not biologically or otherwise undesirable, i.e., without causing an unacceptable level of undesirable biological effects or interacting in a deleterious manner. The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Alkyl" refers to a saturated linear monovalent hydrocarbon moiety of one to twelve, typically one to six, carbon atoms or a saturated branched monovalent hydrocarbon moiety of three to twelve, preferably three to six, carbon atoms. Exemplary alkyl group include, but are not limited to, methyl, ethyl, n-propyl, 2-propyl, tent-butyl, pentyl, and the like.

The term "alkoxy" refers to a moiety of the formula —$OR^1$, where $R^1$ is alkyl as defined herein.

"Alkylene" refers to a saturated linear divalent hydrocarbon moiety of one to twelve, typically one to six, carbon atoms or a branched saturated divalent hydrocarbon moiety of three to twelve, preferably three to six, carbon atoms. Exemplary alkylene groups include, but are not limited to, methylene, ethylene, propylene, butylene, pentylene, and the like.

"Alkylene" refers to a saturated linear divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Alkenyl" refers to a linear monovalent hydrocarbon moiety of two to twelve, typically two to six carbon atoms or a branched monovalent hydrocarbon moiety of three to twelve, typically, three to six carbon atoms, containing at least one double bond. Exemplary alkenyl groups include ethenyl (i.e., vinyl), propenyl, and the like.

"Alkynyl" refers to a linear monovalent hydrocarbon moiety of two to twelve, typically two to six carbon atoms or a branched monovalent hydrocarbon moiety of three to twelve, typically, three to six carbon atoms, containing at least one carbon-carbon triple bond. Exemplary alkenyl groups include ethynyl, propynyl, and the like.

"Aryl" refers to a monovalent mono-, bi- or tricyclic aromatic hydrocarbon moiety of 6 to 15 ring atoms which is optionally substituted with one or more, preferably one, two, or three substituents within the ring structure. When two or more substituents are present in an aryl group, each substituent is independently selected. Exemplary substituents for the aryl group include, but are not limited to, alkyl, haloalkyl, thioalkyl, heteroalkyl, halo, nitro, cyano, cycloalkyl, aryl, heteroaryl, heterocyclyl, haloalkoxy, aryloxy, heteroaryloxy, etc.

"Aralkyl" refers to a moiety of the formula $—R^bR^c$ where $R^b$ is an alkylene group and $R^c$ is an aryl group as defined herein. Exemplary aralkyl groups include, but are not limited to, benzyl, phenylethyl, 3-(3-chlorophenyl)-2-methylpentyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

"Cycloalkyl" refers to a non-aromatic, preferably saturated, monovalent mono- or bicyclic hydrocarbon moiety of three to ten ring carbons. The cycloalkyl can be optionally substituted with one or more, preferably one, two, or three, substituents within the ring structure. When two or more substituents are present in a cycloalkyl group, each substituent is independently selected. Exemplary substituents for cycloalkyl group include, but are not limited to, alkyl, haloalkyl, halo, nitro, cyano, heteroalkyl, aryl, heteroaralkyl, etc.

"Cycloalkylalkyl" refers to a moiety of the formula $—R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, $—CH_2Cl$, $—CF_3$, $—CH_2CF_3$, $—CH_2CCl_3$, and the like.

"Heterocyclyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more, preferably one, two, or three, substituents. When two or more substituents are present in a heterocyclyl group, each substituent is independently selected. Exemplary substituents for heterocyclyl group include, but are not limited to, alkyl, haloalkyl, heteroalkyl, halo, nitro, cyano, aryl, heteroaryl, aralkyl, heteroaralkyl, etc.

"Enantiomeric excess" refers to the difference between the amount of enantiomers. The percentage of enantiomeric excess (% e.e, or % ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

"Diastereomeric excess" refers to the difference between the amount of diastereomers. The percentage of diastereomeric excess (% d.e, or % de) can be calculated by subtracting the percentage of one diastereomer from the percentage of the other diastereomers. For example, if the % de of (R,R)-diastereomer is 99% and % de of all other diastereomers (e.g., (R,S)-, (S,S)- and (S,R)-diastereomers) is 1%, the % de of (R,R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like. Specific examples of leaving groups include, but are not limited to, Cl, Br, I and sulfonate esters such as OMs (mesylate), OTs (tosylate), ONs (nosylate), OTf (triflate) and any other sulfonate esters.

The term "electron withdrawing group" refers an atom or a functional group that removes electron density from a conjugated π system via resonance or inductive electron withdrawal, thus making the π system more electrophilic. Exemplary electron withdrawing groups that are useful in the invention include, but are not limited to, esters, sulfones, aldehydes, nitro groups ($—NO_n$, where n is 1 or 2), nitriles, halides, amides, ketones, heteroaryls, as well as other heteroatom containing functional groups.

The term "α,β-unsaturated compound" refers to any compound that has α,β-unsaturation near the electron withdrawing group. Such a compound can be generally represented as $R^a—CR^b{=}CR^c—Z$, where Z is an electron withdrawing group as defined herein and each of $R^a$, $R^b$ and $R^c$ is independently hydrogen or carbon atom containing group. The α,β-unsaturated compounds of the invention can also have other unsaturated bond(s) that is conjugated to the α,β-unsaturation. Thus, the term α,β-unsaturated compound includes other extended conjugated compounds, such as α,β- and γ,∂-unsaturated compounds as well as other more extended conjugated compounds.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any narrow and/or preferred, more preferred and most preferred definitions, if any.

Compounds of the Invention: Some aspects of the invention provides compounds of the formulas:

I

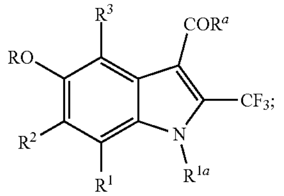

II

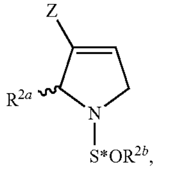

or a pharmaceutically acceptable salt thereof, or a combination thereof, thereby treating the clinical condition associated with locomotor dysfunction in said subject, where * denotes a chiral center; each of R and $R^{3a}$ is independently hydrogen or alkyl; $R^a$ is —$CF_3$, —$OR^{a1}$, or —$NR^{b1}R^{b2}$; $R^{a1}$ is H or alkyl; each of $R^{b1}$ and $R^{b2}$ is independently H or alkyl; $R^{1a}$ is hydrogen, alkyl, or a nitrogen protecting group; each of $R^1$, $R^2$ and $R^3$ is independently hydrogen, alkyl, haloalkyl, halide, vinyl, alkynyl, —CHO, —C(=O)$R^{1b}$ (ketone), —$CO_2R^{1c}$ (ester), —$OR^{1d}$, $OSO_2R^{1e}$, aryl and heteroaryl, wherein each of $R^{1b}$, $R^{1c}$, $R^{1d}$, and $R^{1e}$ is independently alkyl or aryl; $R^{2a}$ is hydrogen, alkyl, haloalkyl, aryl, aralkyl, alkenyl, aralkenyl, cycloalkyl, heteroalkyl, heteroaryl or ester functional group; $R^{2b}$ is alkyl, cycloalkyl, aralkyl, alkenyl, aralkenyl, heteroalkyl, or heteroaryl; and Z is a conjugated electron withdrawing group.

In some embodiments, $R^{1a}$, $R^1$, and $R^3$ are H, $R^2$ is halide, and R is alkyl.

Yet in other embodiments, * is an (R)- or (S)-configuration and $R^{2b}$ is alkyl, Z is an ester, and $R^{2a}$ is alkenyl or heteroaryl. In some instances, the diastereomeric excess of compound of formula II in the composition is at least 90% d.e.

Still in other embodiments, compound of formula II is selected from the group consisting of:

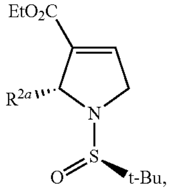

(i)

where $R^{2a}$ is alkenyl; and

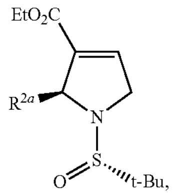

(ii)

where $R^{2a}$ is heteroaryl.

In one particular embodiment, the compound is selected from the group consisting of:

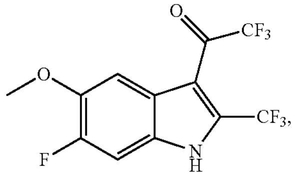

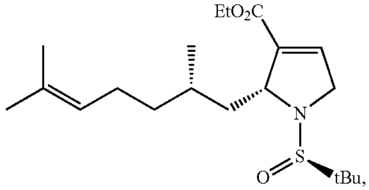

or

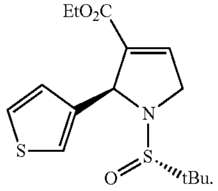

It should be appreciated that combinations of the various groups described herein form other embodiments of compounds of formulas I and II. In this manner, a variety of compounds of formulas I and II are embodied within the present invention as illustrated below.

Compounds of formulas I and II can be produced using methods disclosed in, for example, U.S. patent application Ser. No. 15/329,615, filed Jan. 27, 2017, which has previously been incorporated by reference in its entirety.

One particular method of preparing compound of formula I as disclosed in the above referenced U.S. Patent Application is illustrated in Scheme I.

Scheme I: Exemplary Method of Producing Compound of Formula I
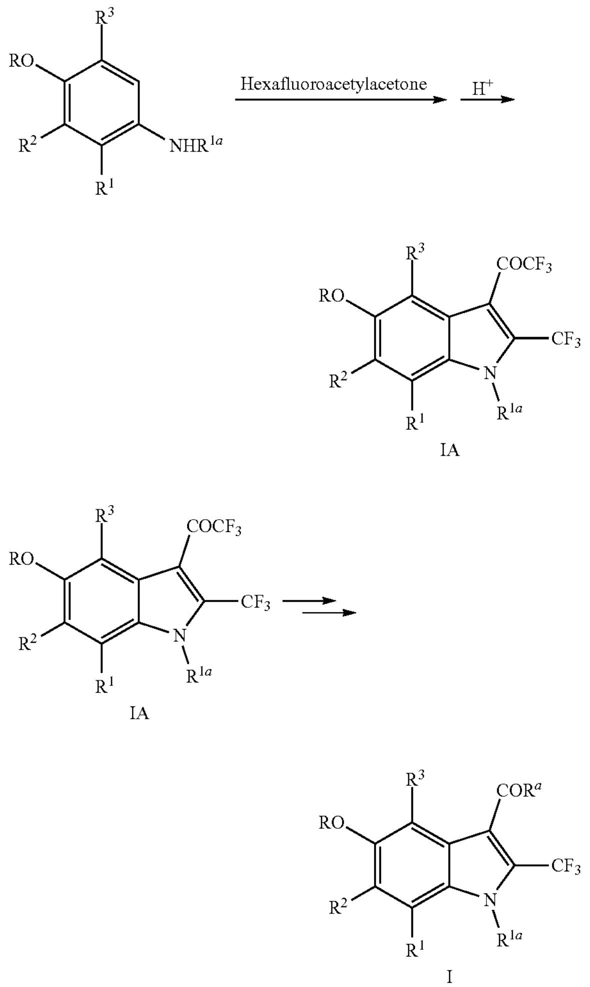
IA
IA
I
where R, $R1^a$, $R^1$, $R^2$, $R^3$, and $R^a$ are those defined herein.
Exemplary compounds of formula I of the invention include, but are not limited to, the following compounds:
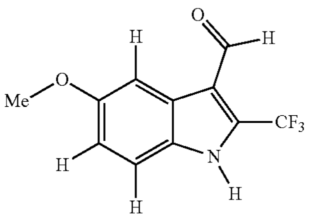
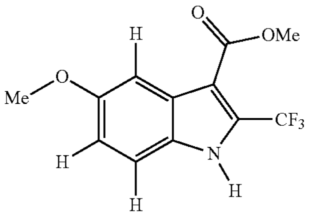
-continued
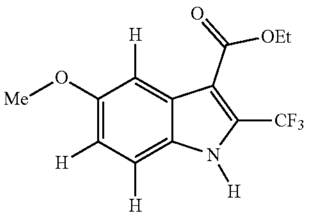
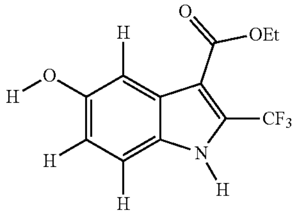
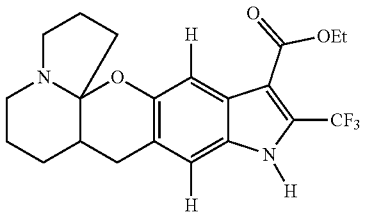
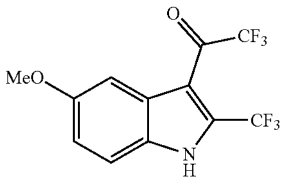
86%
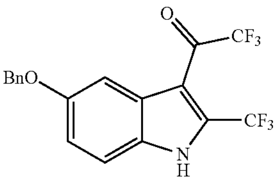
99%
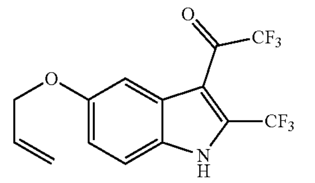
93%
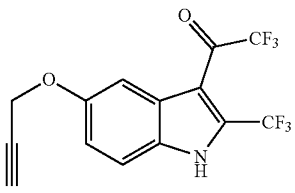
94%

-continued
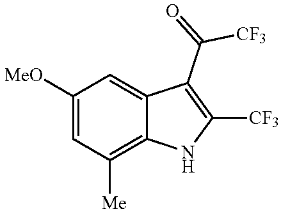
88%
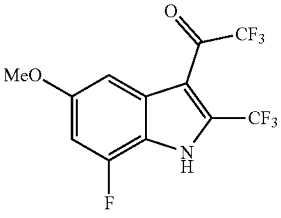
57%
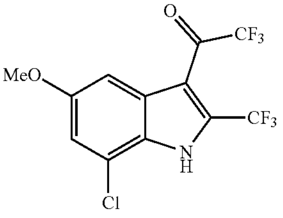
64%
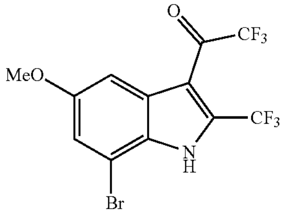
61%
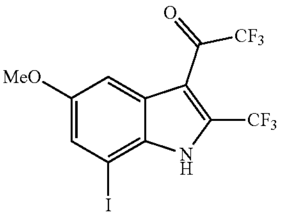
37%
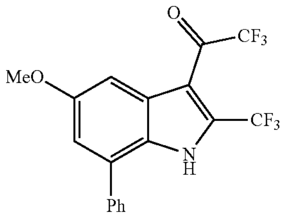
97%
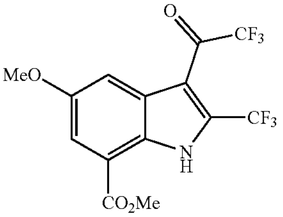
21%
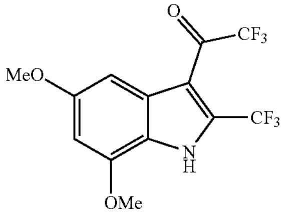
8%
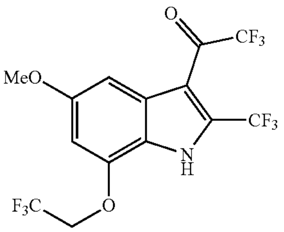
45%
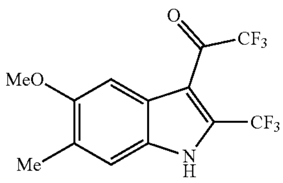
88%
-continued
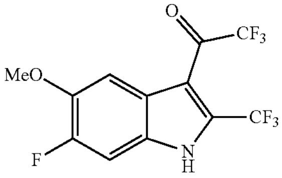
68%
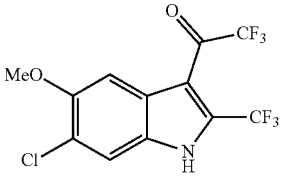
72%
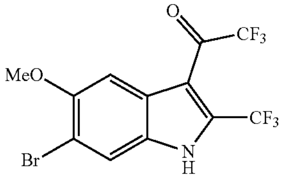
69%
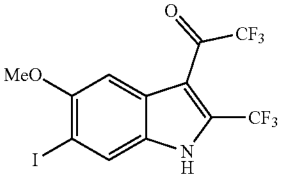
69%
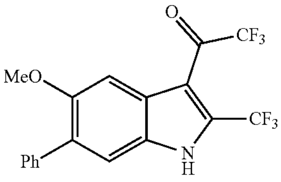
81%
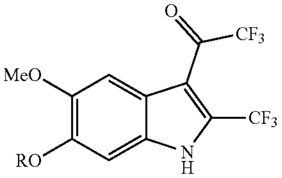
and
64%
1:1 R = Ac, R = H
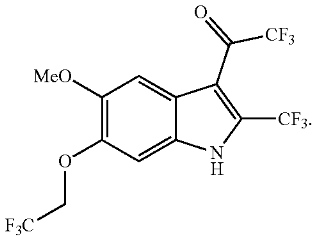
70%

One particular general method of producing compounds of formula II is illustrated in Scheme II below.
Scheme II: Exemplary Method of Producing Compound of Formula II
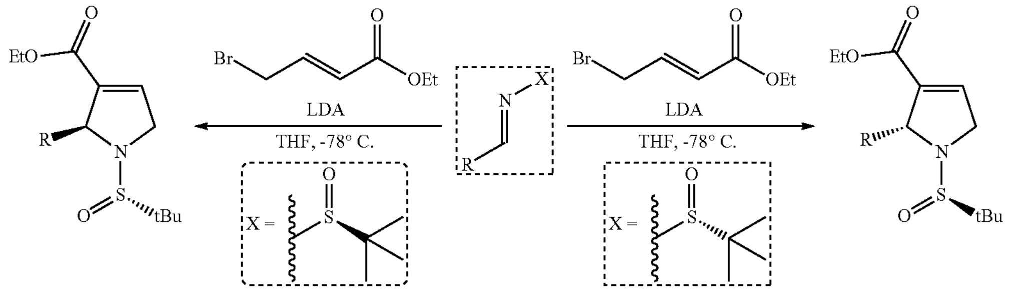
Exemplary compounds of formula II encompassed within the scope of the present invention include, but are not limited to, the following representative compounds:
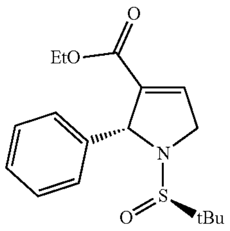
52%
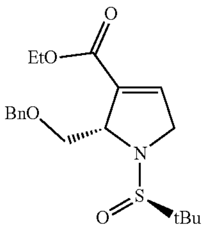
77%
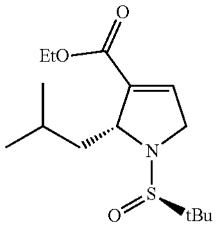
56%
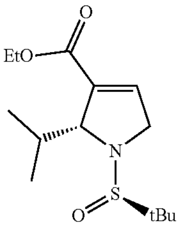
52%
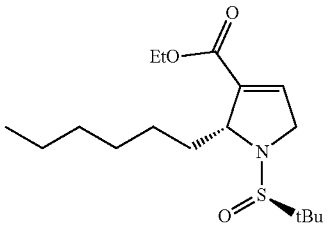
55%
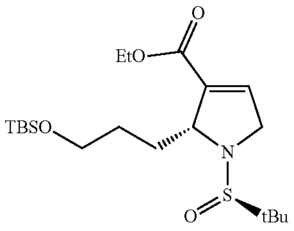
53%
-continued
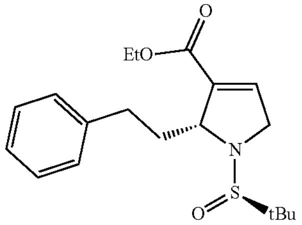
69%
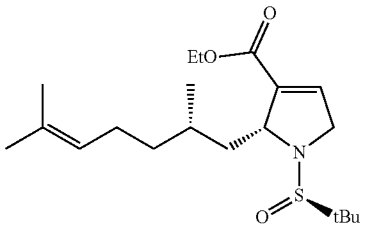
59%
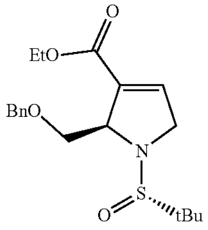
75%
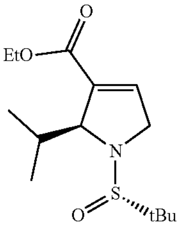
55%
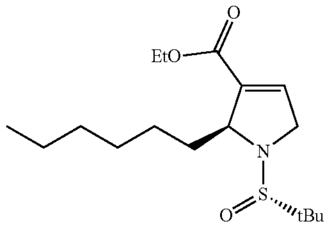
56%

-continued

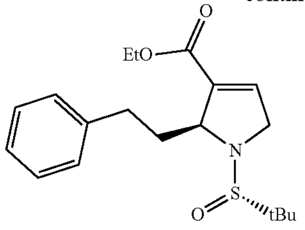

68%

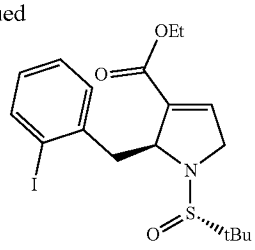

58%

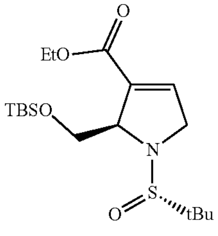

75%

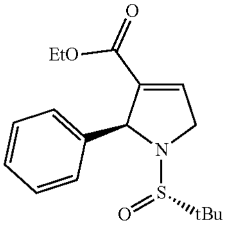

50%

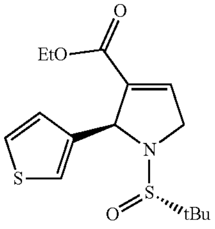

63%

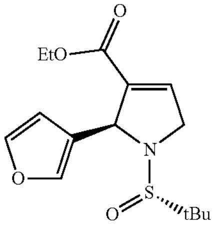

56%

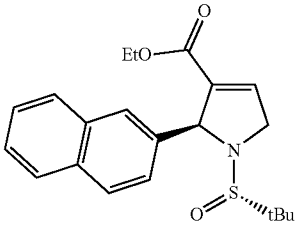

63%

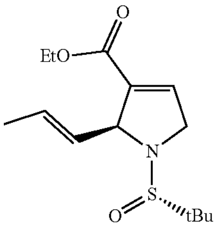

51%

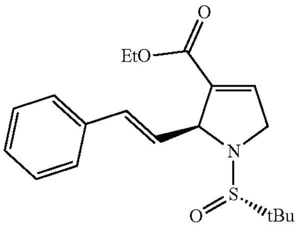

56%

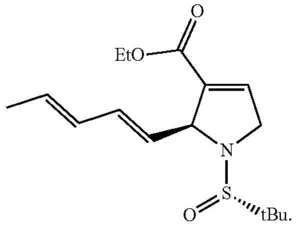

58%

The compounds disclosed herein can, depending on their structure, exist in stereoisomeric forms (e.g., enantiomers, diastereomers, including those in the case of atropisomers). In particular, compounds of formula II have at least two stereocenters. Accordingly, in some embodiments, diastereomeric excess of compound of the invention is at least about 80% d.e., typically at least about 85% d.e., often at least about 90% d.e., more often at least about 95% d.e., and most often at least about 98% d.e.

Salts are physiologically acceptable salts of the compounds disclosed herein. Physiologically acceptable salts of the compounds disclosed herein include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Administration and Pharmaceutical Composition: The compounds described herein can be used in mitigating locomotor dysfunction, reducing TDP-43 aggregation or toxicity, ameliorating one or more symptoms associated with ALS, or to decrease the release of glutamate.

Compounds and compositions disclosed herein can also be used for the treatment of one or more neurodegenerative diseases. The compounds disclosed herein can be used to prevent a neurodegenerative disease, ameliorating one or more symptoms associated with one or more neurodegenerative diseases, or to decrease the release of glutamate.

Accordingly, another aspect of the invention includes pharmaceutical compositions for treating a various clinical conditions associated with a neurodegenerative disease or locomotor dysfunction in a subject. The pharmaceutical compositions disclosed herein comprise at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual) or parenteral (including intramuscular, intraarterial, intrathecal, subcutaneous and intravenous) administration or in a form suitable for administration by inhalation or insufflation. Typical manner of administration is generally oral or parenteral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term “preparation” is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula (I), as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula (I) or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound disclosed herein, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Utility: Compositions and compounds of the invention are useful in treating a variety of clinical conditions such as, but not limited to, a neurodegenerative disease and locomotor dysfunction. Exemplary neurodegenerative diseases that can be treated using a composition and/or a compound of the invention include, but are not limited to, Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, transient ischemic attack, encephalopathy, and traumatic brain injury (TBI).

Amyotrophic Lateral Sclerosis (ALS): ALS is a rapidly progressing neurodegenerative disease with currently no curative treatment. Using a previously developed a *Drosophila* (fruit fly) model of ALS, compounds of the invention were identified that can reduce the locomotor dysfunction associated with the disease. Results show that these compounds mitigate TDP-43 proteinopathy which is present in 97% of ALS patients, 45% of FTD patients and a growing number of patients with related neurodegenerative disorders including Alzheimer's PD, etc. TDP-43 proteinopthy manifests in part as mislocalization to the cytoplasm (sometimes accompanied by aggregation) is one of the characteristics of ALS and FTD.

Amyotrophic lateral sclerosis (ALS) is a rapidly progressive, invariably fatal neurological disease that attacks the neurons responsible for controlling voluntary muscles, such as those in the arms, legs and face. ALS causes weakness with a wide range of disabilities. Eventually, all muscles under voluntary control are affected, and individuals lose their strength and the ability to move their arms, legs, and body. When muscles in the diaphragm and chest wall fail, people lose the ability to breathe without ventilatory support. Most people with ALS die from respiratory failure, usually within 3 to 5 years from the onset of symptoms. However, about 10 percent of those with ALS survive for 10 or more years.

Currently no cure that can reverse the damage of ALS exists. The drugs riluzole (Rilutek®, Sanofi) and Radicava™ (edaravone) are the only medications approved by the FDA for ALS. Without being bound by any theory, it is believed that riluzole reduces damage to motor neurons by decreasing glutamate toxicity at synapses while edaravone is believed to act as a free radical scavenger although its mechanism of action in ALS remains unknown. Neither Riluzole nor Radicava, however, can reverse the damage already done to motor neurons, and persons taking the drug must be monitored for liver damage and other possible side effects. ALS has a high level of unmet need, given that an optimal course of therapy can extend a patient's survival by only a few months.

Other marketed products used as treatments for ALS include baclofen, trihexyphenidyl hydrochloride, morphine sulfate, lorazepam, glycopyrrolate, benztropine mesylate, gabapentin, Valium® (diazepam), tizanidine, phenytoin sodium, Elavil® (amitriptyline hydrochloride), Cogentin® (benztropine mesylate), ReQuip®, Robinul® (glycopyrrolate), Cuvposa® (glycopyrrolate), Atropine sulphate, Luvox® (fluvoxamine maleate), Dantrium® (dantrolene sodium), Dilantin® (phenytoin sodium), Neurontin® (gabapentin), morphine sulfate and dexpramipexole.

While multiple drugs have shown promise in preclinical in vitro and in vivo models of ALS, they have failed to show efficacy in human trials. These include glutamate antagonists other than riluzole, neurotrophic factors, antiapoptotic agents, antioxidants, and immunomodulatory drugs.

TDP-43: TDP-43 is a conserved RNA binding protein involved in several cellular processes. TDP-43 has been initially identified as a nucleic acid binding protein that regulates HIV gene expression by binding to its TAR DNA element, hence its original name, TAR DNA Binding Protein (TARDP). TDP-43 is ubiquitously expressed and co-localizes with SMN proteins in the nucleus. Its cellular functions include transcriptional repression, splicing, miRNA biogenesis, apoptosis and cell division. TDP-43 associates with RNA granules and co-purifies with β-actin and CaMKII mRNAs in cultured neurons. TDP-43 co-localizes with Fragile X protein and Staufen in an activity dependent manner, indicating that it can regulate synaptic plasticity in vivo by controlling the transport, splicing and translation of synaptic mRNAs. TDP-43 protein consists of two RNA recognition motifs (RRM1 and 2) as well as a Glycine-rich domain within the C terminus. In vitro assays have demonstrated that TDP-43 binds with high affinity UG-rich sequences, consistent with its role in mRNA splicing.

Pathological studies have identified the RNA binding protein TDP-43 as a component of cytoplasmic aggregates in neurons, glia and muscles, in ALS as well as Fronto-Temporal Lobar Degeneration, Alzheimer's and Inclusion Body Myositis. TDP-43's cellular functions are complex and reflect its ability to regulate several RNA targets at the level of splicing, transport and translation. Recently, several TDP-43 mutations have been identified in ALS patients. Given its presence in cytoplasmic inclusions and the identification of several mutations linked to motor neuron degeneration, TDP-43 has emerged as a common denominator for a significant fraction of ALS cases known to date. TDP-43's ability to form aggregates, induce apoptosis and splicing function can be used as secondary assays.

Most TDP-43 mutations found in ALS patients represent amino acid substitutions that are thought to increase TDP-43 phosphorylation and target it for degradation. Evidence has been provided that these missense mutations mimic a loss of nuclear function and a gain of cytoplasmic function for TDP-43, and that the RNA binding domain is required to mediate neurotoxicity. Given its presence in cytoplasmic inclusions and the identification of several mutations linked to neural degeneration, TDP-43 has emerged as a common denominator for the majority of ALS cases known to date. Thus, studies using this model of ALS based on TDP-43 can provide widely applicable insights into this disease.

In recent years, the fruit fly *Drosophila* has emerged as a premiere genetic model for studying human disease. Using loss of function mutations in *Drosophila* TDP-43 (dTDP-43) as well as RNAi knock-down approaches, alterations were identified in the architecture of the larval neuromuscular junction, locomotor defects and retina neurodegeneration in adults. To further establish a *Drosophila* model, transgenics were generated expressing wild-type and mutant forms of fly and human TDP-43, which mimic the mutations found in human patients. Experiments show that overexpression of TDP-43 results in the formation of cytoplasmic aggregates, neuronal loss and locomotor defects. Taken together, these data indicate that loss of function for TDP-43 as well as overexpression of wild-type and mutant TDP-43 in *Drosophila* recapitulate several aspects of the disease pathology. Furthermore, immunolocalization and genetic rescue data indicate a loss of function mechanism for the disease. The defects due to altered TDP-43 function can be corrected by genetic and pharmacological intervention and the genes/compounds that rescue the TDP-43 phenotypes can provide new therapeutic approaches for ALS. Genetic screens have identified a number of candidate genomic regions that rescue the retinal degeneration due to TDP-43 misexpression in the eye and/or locomotor dysfunction caused by TDP-43 proteinopathy.

Since TDP-43 is involved in the pathology of a majority of ALS cases and has recently been shown to also be a cause for the disease, studies of a TDP-43 based model can provide insights into a wide spectrum of ALS cases. There is data indicating that in flies, alterations in TDP-43 function lead to defects in neuromuscular junction architecture, adult locomotion and neurodegeneration. Several transgenic lines expressing wild-type and mutant forms of dTDP-43 and human TDP-43 (huTDP-43) that correspond to mutations found in human patients have been developed. Overexpression of these transgenes leads to the formation of cytoplasmic inclusions and leads to neuronal dysfunction and death. The data demonstrates that the fly model recapitulates several aspects of ALS pathology. Genetic screens can identify single gene mutations that can rescue or enhance the TDP-43 phenotypes. These genes can provide insights into the molecular mechanisms involved in ALS and may represent novel therapeutic targets. In addition, this approach has the potential to identify ALS loci that are yet to be discovered in human patients. TDP-43-based phenotypes can be used to screen for compounds that rescue the neuroanatomical and functional defects in the fly model. It should be noted that this fly model has been validated in human samples.

It has been shown that ALS can be successfully modeled in *Drosophila* using both loss of function and gain of function approaches. Transgenic lines, wild-type and several mutant forms of both the fly and human proteins, which can be expressed specifically in motor neurons and the eye neuroepithelium using the Gal4-UAS system have been produced. Phenotypic analyses including testing for cytoplasmic inclusions, neuroanatomical and functional studies can determine the extent to which different alterations in TDP-43 recapitulate the pathology associated with the human disease.

ALS is a group of complex motor neuron diseases involving a dozen distinct and overlapping protein inclusions, including TAR DNA-binding protein-43 (TDP-43). TDP-43 is found in 97% of patients with ALS. Described herein are results using a recently developed *Drosophila* (fruit fly) model for ALS, by expressing human transactive response DNA-binding protein 43 kDA (TAR DNA-binding protein 43, TDP-43) to test the compounds disclosed herein. TDP-43 is involved in RNA processing, including splicing, transcription, translation and transport. The primary histopathological feature in a major subset of ALS cases is the inclusion of TDP-43 in the cytoplasm of upper and lower motor neurons and in other regions of the central nervous system. While TDP-43 aggregation (or toxicity) is a hallmark of most of the ALS cases, it is also found in neurodegenerative disorders, including frontotemporal dementia and Alzheimer's disease.

Protein aggregation is a pathology characteristic of ALS. SOD1 was the first protein to be identified to aggregate in familial ALS cases carrying a mutation in SOD1 gene. Due to exponential development of genetic techniques, several new proteins have been identified to be involved in ALS pathophysiology during the past few years, including TDP-43, FUS, OPTN, UBQLN2 and C9ORF72.

In some aspects of the invention, compounds and compositions disclosed herein can be used to target TDP-43 aggregation or toxicity for treatment of ALS and neurodegenerative diseases. In some embodiments, the compounds and compositions described herein target TDP-43 and may be useful neuroprotective agents for TDP-43 proteinopathies.

As stated herein, the compounds disclosed herein can be used to treat one or more neurodegenerative diseases, including but not limited to Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, and transient ischemic attack.

In an aspect, the compounds or compositions described herein further comprise a detectable label. Detectable labels include, but are not limited to, any detectable moiety, including, for example, fluorescent labels, radioactive labels, and electronic labels. In an aspect, the labels can be used to detect or identify TDP-43 in the plasma, cerebrospinal fluid, brain, spinal cord or other samples. In an aspect, detecting and monitoring levels or aggregation (or toxicity) of TDP-43 in ALS or other neurodegenerative diseases can provide the ability to diagnose and distinguish TDP-43 proteinopathies from other clinically similar neurodegenerative diseases (e.g., tauopathies or other proteinopathies). Further, detection of and/or quantification of TDP-43 neuropathology in living patients can also provide a diagnosis and the ability to monitor the response of patients having a neurodegenerative TDP-43 proteinopathy to disease-modifying therapies. In an aspect, the detectable label can be used to detect the presence of TDP-43 in a sample in which a compound specifically binds TDP-43.

Disclosed herein are methods of using one or more the compounds disclosed herein for the treatment or prevention of diseases or disorders, including one or more of the diseases or disorders described above.

Also disclosed herein are methods of mitigating locomotor dysfunction in a subject in need thereof. The methods include the step of administering to the subject a therapeutically effective amount of at least one compound of formula I or II or a pharmaceutically acceptable salt thereof. In some embodiments, the method utilizes at least one compound of the formula:

(i)

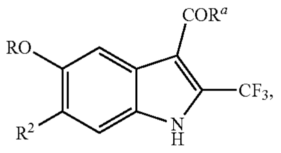

where R is alkyl, $R^2$ is halide and $R^a$ is —$CF_3$, —$OR^{a1}$, or —$NR^{b1}R^{b2}$, where $R^{a1}$, $R^{b1}$, and $R^{b2}$ are those defined herein;

(ii)

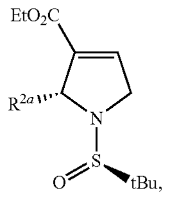

where $R^{2a}$ is alkenyl; or (iii)

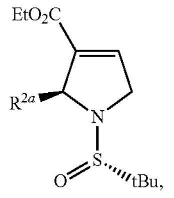

where $R^{2a}$ is heteroaryl, or a pharmaceutically acceptable salt thereof. In one specific embodiment, the method utilizes at least one compound of the formula:

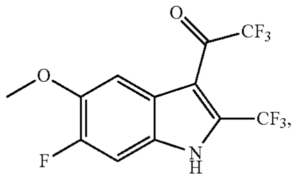

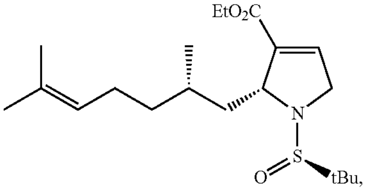

or

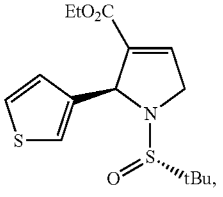

or a pharmaceutically acceptable salt thereof.

Disclosed herein are methods of reducing TDP-43 aggregation or toxicity in a subject in need thereof. The methods include the step of administering to the subject a therapeutically effective amount of at least one compound of formula I or II, or a pharmaceutically acceptable salt thereof, thereby reducing TDP-43 aggregation or toxicity in the subject. In an aspect, the TDP-43 expression is not reduced, i.e., as compared to the TDP-43 expression level prior to administration of a compound of the invention. It should be appreciated that the term "not reduced" means there is no statistically significant difference in TDP-43 expression level. In some embodiments, the method utilizes at least one compound of the formula:

(i)

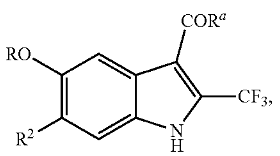

where R is alkyl, $R^2$ is halide and $R^a$ is —$CF_3$, —$OR^{a1}$, or $NR^{b1}R^{b2}$, where $R^{a1}$, $R^{b1}$, and $R^{b2}$ are those defined herein;

(ii)

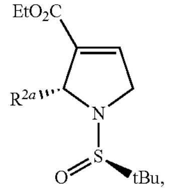

where $R^{2a}$ is alkenyl; or (iii)

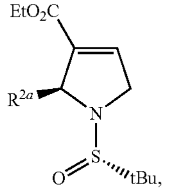

where $R^{2a}$ is heteroaryl, or a pharmaceutically acceptable salt thereof. In one specific embodiment, the method utilizes at least one compound of the formula:

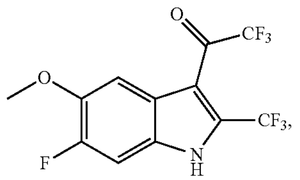

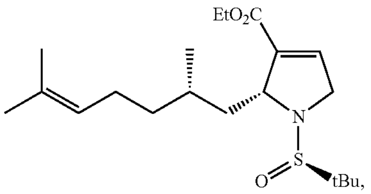

or

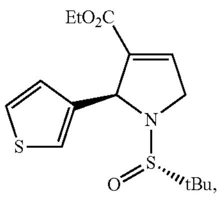

or a pharmaceutically acceptable salt thereof.

Another aspect of the invention provides a method for treating ALS in a subject in need thereof. The methods include the step of administering to the subject a therapeutically effective amount of at least one compound of formula I or II, or a pharmaceutically acceptable salt thereof, thereby treating ALS in the subject. In some embodiments, the method utilizes at least one compound of the formula:

(i)

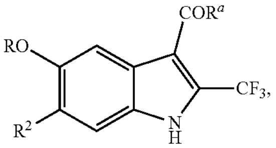

where R is alkyl, $R^2$ is halide and $R^a$ is —$CF_3$, —$OR^{a1}$, or —$NR^{b1}R^{b2}$, where $R^{a1}$, $R^{b1}$, and $R^{b2}$ are those defined herein;

(ii)

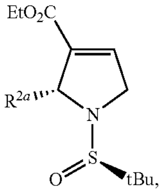

where $R^{2a}$ is alkenyl; or (iii)

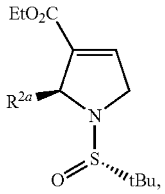

where $R^{2a}$ is heteroaryl, or a pharmaceutically acceptable salt thereof. In one specific embodiment, the method utilizes at least one compound of the formula:

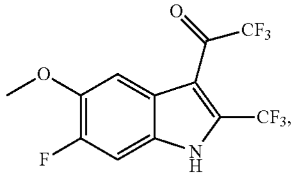

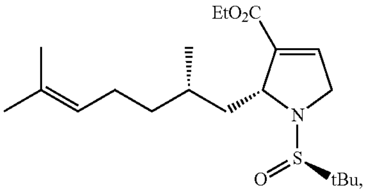

or

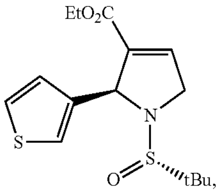

or a pharmaceutically acceptable salt thereof.

Yet another aspect of the invention provides methods for ameliorating a symptom associated with ALS in a subject in need thereof. The methods include the step of administering to the subject a therapeutically effective amount of at least one compound of formula I or II, or a pharmaceutically acceptable salt thereof, thereby ameliorating a symptom associated with ALS in the subject. In some embodiments, the method utilizes at least one compound of the formula:

(i)

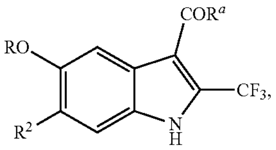

where R is alkyl, $R^2$ is halide and $R^a$ is —$CF_3$, —$OR^{a1}$, or $NR^{b1}R^{b2}$, where $R^{a1}$, $R^{b1}$, and $R^{b2}$ are those defined herein;

(ii)

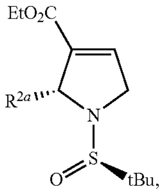

where $R^{2a}$ is alkenyl; or (iii)

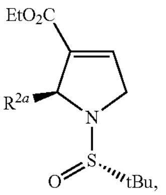

where $R^{2a}$ is heteroaryl, or a pharmaceutically acceptable salt thereof. In one specific embodiment, the method utilizes at least one compound of the formula:

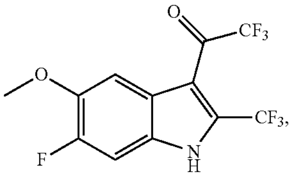

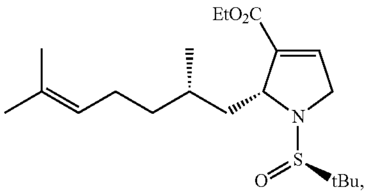 or

-continued

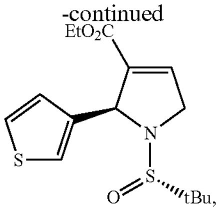

or a pharmaceutically acceptable salt thereof.

Still yet another aspect of the invention provides a method for treating a neurodegenerative disease in a subject in need thereof. The methods include the step of administering to the subject a therapeutically effective amount of at least one compound of formula I or II, or a pharmaceutically acceptable salt thereof, thereby treating a neurodegenerative disease in the subject. In some embodiments, the method utilizes at least one compound of the formula:

(i)

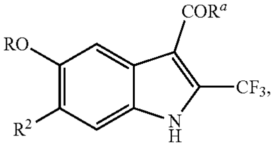

where R is alkyl, $R^2$ is halide and $R^a$ is —$CF_3$, —$OR^{a1}$, or —$NR^{b1}R^{b2}$, where $R^{a1}$, $R^{b1}$, and $R^{b2}$ are those defined herein;

(ii)

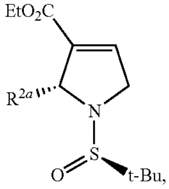

where $R^{2a}$ is alkenyl; or (iii)

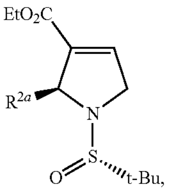

where $R^{2a}$ is heteroaryl, or a pharmaceutically acceptable salt thereof. In one specific embodiment, the method utilizes at least one compound of the formula:

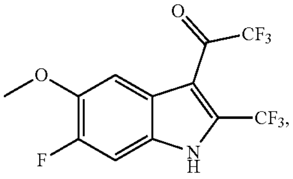

-continued

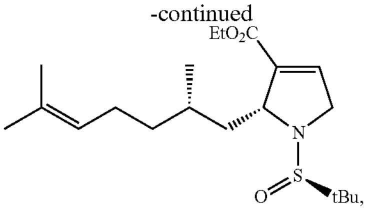

or

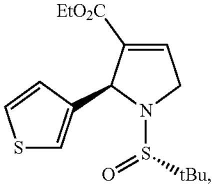

or a pharmaceutically acceptable salt thereof.

In some embodiments, the neurodegenerative disease is selected from the group consisting of Alzheimer's disease, frontotemporal dementia, FTLD-U (a frontotemporal dementia caused by mutations in progranulin protein), amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, and transient ischemic attack, or any combination thereof.

Another aspect of the invention provides methods for preventing a neurodegenerative disease in a subject in need thereof. The methods include the step of administering to the subject a therapeutically effective amount of at least one compound of formula I or II, or a pharmaceutically acceptable salt thereof, thereby preventing a neurodegenerative disease in the subject. In some embodiments, the method utilizes at least one compound of the formula:

(i)

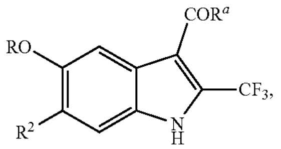

where R is alkyl, $R^2$ is halide and $R^a$ is —$CF_3$, —$OR^{a1}$, or —$NR^{b1}R^{b2}$, where $R^{a1}$, $R^{b1}$, and $R^{b2}$ are those defined herein;

(ii)

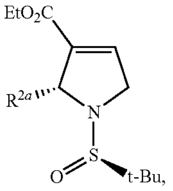

where $R^{2a}$ is alkenyl; or (iii)

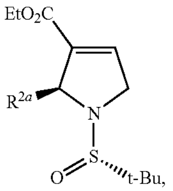

where $R^{2a}$ is heteroaryl, or a pharmaceutically acceptable salt thereof. In one specific embodiment, the method utilizes at least one compound of the formula:

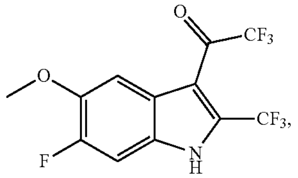

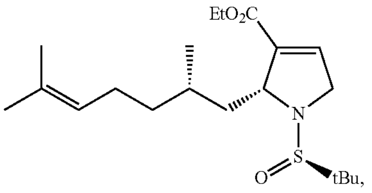

or

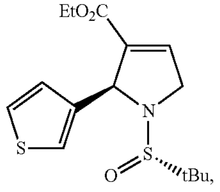

or a pharmaceutically acceptable salt thereof.

In yet another aspect of the invention, in any of the methods disclosed herein, the methods can further comprise administering a therapy that relieves one or more symptoms associated with a clinical condition to be treated. As an example, symptoms of ALS include but are not limited to stiff muscles, muscle twitching, muscle weakness due to muscles decreasing in size, difficulty speaking, swallowing and breathing. Thus, a method for treating ALS disclosed herein can also include a combination therapy in which a therapy (or a compound) that decreases the release of glutamate can be co-administered either simultaneously or separately. In one particular embodiment, in any of the methods disclosed herein, the methods can further comprise administering a compound that decreases the release of glutamate to the subject. In another embodiment of the invention, in any of the methods disclosed herein, the methods can further comprise administering to the subject one or more of baclofen, trihexyphenidyl hydrochloride, morphine sulfate, lorazepam, glycopyrrolate, benztropine mesylate, gabapentin, Valium® (diazepam), tizanidine, phenytoin sodium, Elavil® (amitriptyline hydrochloride), Cogentin® (benztropine mesylate), ReQuip®, Robinul® (glycopyrrolate), Cuvposa® (glycopyrrolate), Atropine sulphate, Luvox® (fluvoxamine maleate), Dantrium® (dantrolene sodium), Dilantin® (phenytoin sodium), Neurontin® (gabapentin), morphine sulfate and dexpramipexole.

In some embodiments, the subject is a mammal. In one particular embodiment, the mammal is a human.

The compounds disclosed herein can be used alone or, if required, in combination with other active compounds. Accordingly, disclosed herein are medicaments comprising at least one of the compounds described herein and one or more further active compounds for the treatment and/or prevention of one or more of the diseases or disorders mentioned above. Suitable active compounds for combinations are one or more of baclofen, trihexyphenidyl hydrochloride, morphine sulfate, lorazepam, glycopyrrolate, benztropine mesylate, gabapentin, Valium® (diazepam), tizanidine, phenytoin sodium, Elavil® (amitriptyline hydrochloride), Cogentin® (benztropine mesylate), ReQuip®, Robinul® (glycopyrrolate), Cuvposa® (glycopyrrolate), Atropine sulphate, Luvox® (fluvoxamine maleate), Dantrium® (dantrolene sodium), Dilantin® (phenytoin sodium), Neurontin® (gabapentin), morphine sulfate and dexpramipexole.

Disclosed herein are medicaments comprising at least one compound described herein, usually in combination with one or more inert, non-toxic, pharmaceutically suitable excipients, and their use for the purposes mentioned above. The compounds according to the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or optic route or as implant or stent.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1: Improvement of Locomotor Function

Figure 2:
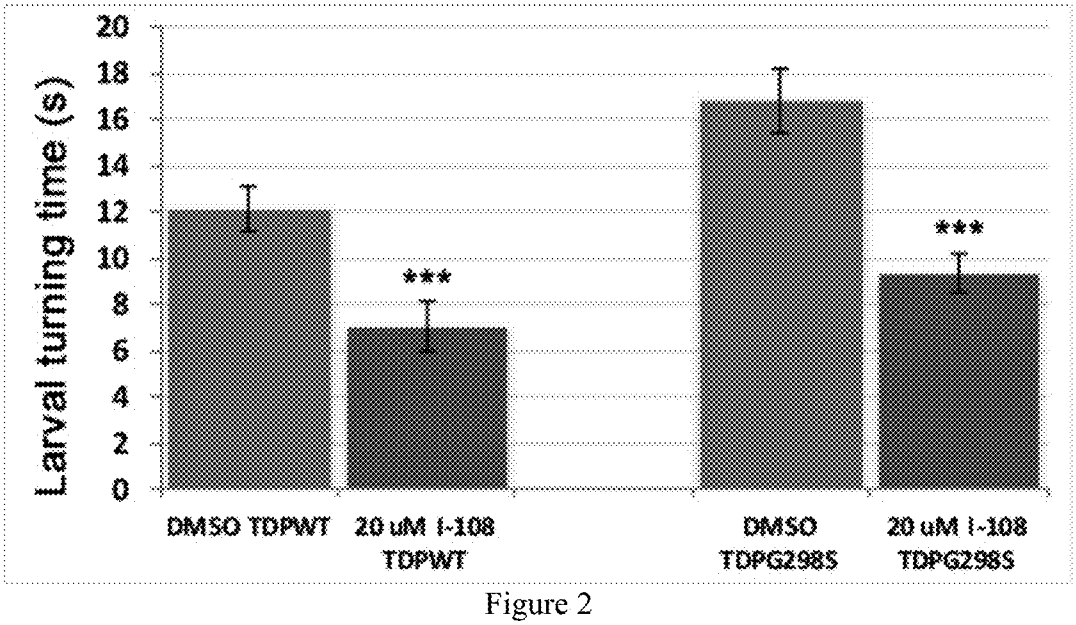
FIG. 2 shows compound CH-I-108 improves locomotor function in larvae expressing either TDPWT of TDPG298S in motor neurons. Student's t-test was used to evaluate statistical significance (***=$P_{value}$0.001; N>20 larvae/genotype).
Figure 3:
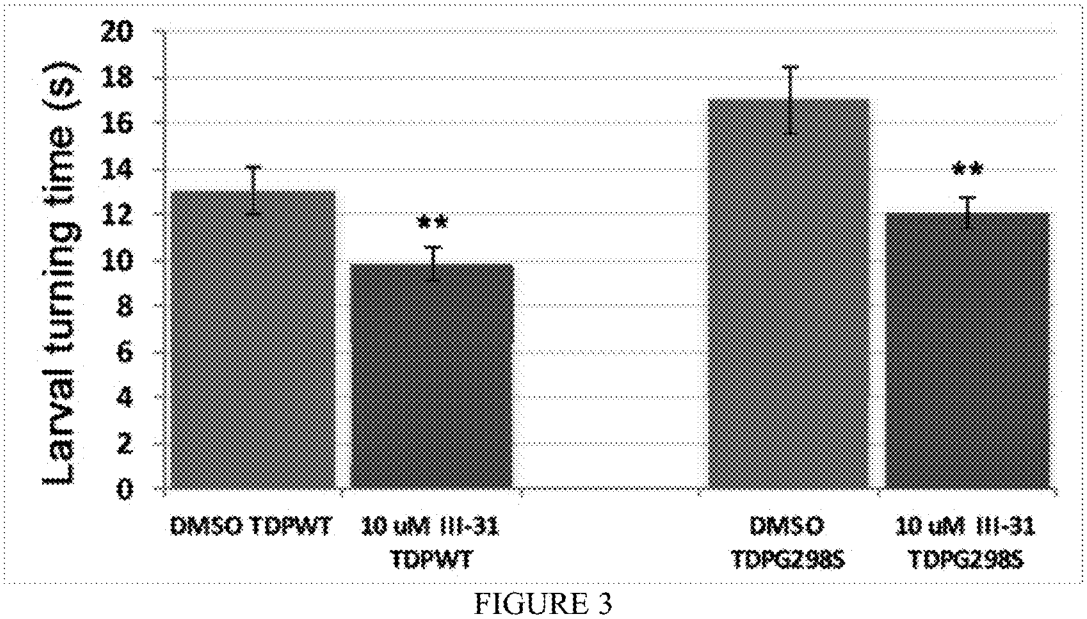
FIG. 3 shows compound CH-III-31 improves locomotor function in larvae expressing either TDPWT of TDPG298S in motor neurons. Student's t-test was used to evaluate statistical significance (***=$P_{value}$<0.001; N>20 larvae/genotype).

The compounds were first assessed for their effect on viability and the four structures included in this application exhibited improved adult survival when TDP-43 was expressed in motor neurons. Notably, these compounds do not affect control larvae and do not appear to affect TDP-43 levels or solubility. The top four promising compounds were further tested for their ability to improve locomotor function. As shown in FIGS. 1-3, administration of EV-3-298, CH-I-108, and CH-III-31 resulted in significant improvement of locomotor function measured by larval turning assays.

Materials and Methods

*Drosophila* genetics. TDP-43 was expressed in motor neurons using the GAL4-UAS bipartite expression system. D42 GAL4 was used as an expression driver and UAS-TDP-43 YFP trasgenics were used as responder lines (Estes, et al., 2011, Hum. Mol. Genet).

Locomotor function. Locomotion was assessed using quantitative larval turning assays. Crosses were carried out at 25° C. and wandering third instar larvae were placed on a grape juice plate at room temperature. After a 30 second acclimation period, larvae were gently turned ventral side up. They were observed until they turned over (dorsal side up) and began making a forward motion. The time it took to complete this task was recorded for at least 20 larvae per genotype.

Statistical analyses. Student's t-tests were performed to determine statistical significance.

RESULTS

Larval turning assays (performed as described in Materials and methods) show that locomotor function was significantly improved (see FIGS. 1-4). Notably, these compounds did not affect control larvae and did not appear to affect TDP-43 levels or solubility (data not shown).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for curing, ameliorating, stabilizing, or mitigating a clinical condition associated with a neurodegenerative disease or locomotor dysfunction in a subject, said method comprising administering to the subject in need of such a treatment a therapeutically effective amount of a compound of the formula:

I

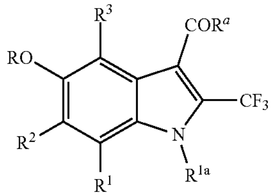

or

II

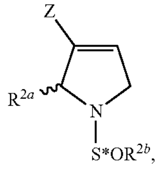

or a pharmaceutically acceptable salt thereof, or a combination of the compound thereof, thereby curing, ameliorating, stabilizing, or mitigating the clinical condition associated with locomotor dysfunction in said subject, wherein

* denotes a chiral center;

R is hydrogen or alkyl;

$R^a$ is —$CF_3$, —$OR^{a1}$, or —$NR^{b1}R^{b2}$;

$R^{a1}$ is H or alkyl;

each of $R^{b1}$ and $R^{b2}$ is independently H or alkyl;

$R^{1a}$ is hydrogen, alkyl, or a nitrogen protecting group;

each of $R^1$, $R^2$ and $R^3$ is independently hydrogen, alkyl, haloalkyl, halide, vinyl, alkynyl, —CHO, —C(═O)

$R^{1b}$ (ketone), —$CO_2R^{1c}$ (ester), —$OR^{1d}$, $OSO_2R^{1e}$, aryl and heteroaryl, wherein each of $R^{1b}$, $R^{1c}$, $R^{1d}$ and $R^{1e}$ is independently alkyl or aryl;

$R^{2a}$ is hydrogen, alkyl, haloalkyl, aryl, aralkyl, alkenyl, aralkenyl, cycloalkyl, heteroalkyl, heteroaryl or ester functional group;

$R^{2b}$ is alkyl, cycloalkyl, aralkyl, alkenyl, aralkenyl, heteroalkyl, or heteroaryl; and Z is a conjugated electron withdrawing group.

2. The method of claim 1, wherein said neurodegenerative disease is selected from the group consisting of Alzheimer's disease, frontotemporal dementia, a frontotemporal dementia caused by mutations in progranulin protein, amyotrophic lateral sclerosis (ALS), Huntington's chorea, Creutzfeld-Jacob disease, trinucleotide repeat diseases, cerebral degenerative diseases presenile dementia, senile dementia, Parkinsonism linked to chromosome 17 (FTDP-17), progressive supranuclear palsy (PSP), Huntington's disease (HD), Pick's disease, primary progressive aphasia, corticobasal dementia, Parkinson's disease, Parkinson's disease with dementia, dementia with Lewy bodies, Down's syndrome, multiple system atrophy, spinal muscular atrophy (SMA), spinocerebellar ataxia, spinal degenerative disease/motor neuron degenerative diseases, Hallervorden-Spatz syndrome, cerebral infarct, cerebral trauma, chronic traumatic encephalopathy, transient ischemic attack, encephalopathy, traumatic brain injury (TBI), and any combination thereof.

3. The method of claim 1, wherein said clinical condition comprises Amyotrophic Lateral Sclerosis (ALS), frontotemporal degeneration (FTD), Alzheimer's Disease, encephalopathy, or traumatic brain injury (TBI).

4. The method of claim 3, wherein said FTD comprises frontotemporal lobar degeneration with ubiquitinated inclusions.

5. The method of claim 3, wherein said method comprises ameliorating a symptom associated with ALS.

6. The method of claim 1 further comprising administering a therapy that relieves a symptom associated with ALS.

7. The method of claim 1 further comprising administering a compound that decreases release of glutamate to the subject.

8. The method of claim 7, wherein said compound that decreases the release of glutamate comprises riluzole.

9. The method of claim 1 further comprising administering to said subject a compound selected from the group consisting of baclofen, trihexyphenidyl hydrochloride, morphine sulfate, lorazepam, glycopyrrolate, benztropine mesylate, gabapentin, diazepam, tizanidine, phenytoin sodium, amitriptyline hydrochloride, ropinirole, Atropine sulphate, fluvoxamine maleate, dantrolene sodium, morphine sulfate, dexpramipexole, and a combination of two or more compounds thereof.

10. The method of claim 1, wherein said method comprises administering to the subject a therapeutically effective amount of a compound of the formula:

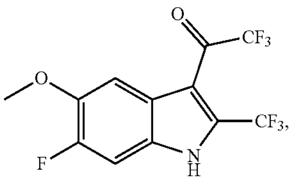

-continued

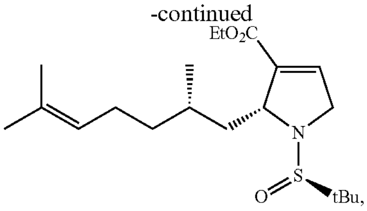

or

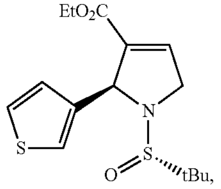

or a combination of the compound thereof.

11. A method for reducing TDP-43 toxicity in a subject, said method comprising the step of administering to the subject a therapeutically effective amount of at least one compound selected from the group consisting of:

I

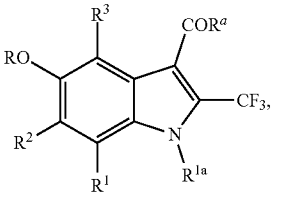

or

II

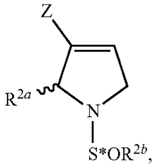

or a pharmaceutically acceptable salt thereof, thereby reducing TDP-43 toxicity in said subject, wherein

* denotes a chiral center;

R is hydrogen or alkyl;

$R^a$ is —$CF_3$, —$OR^{a1}$, or —$NR^{b1}R^{b2}$;

$R^{a1}$ is H or alkyl;

each of $R^{b1}$ and $R^{b2}$ is independently H or alkyl;

X is —$NR^{1a}$—, wherein $R^{1a}$ is hydrogen, alkyl or a nitrogen protecting group;

each of $R^1$, $R^2$ and $R^3$ is independently hydrogen, alkyl, haloalkyl, halide, vinyl, alkynyl, —CHO, —C(═O)$R^{1b}$ (ketone), —$CO_2R^{1c}$ (ester), —$OR^{1d}$, $OSO_2R^{1e}$, aryl and heteroaryl, wherein each of $R^{1b}$, $R^{1c}$, $R^{1d}$ and $R^{1e}$ is independently alkyl or aryl;

$R^{2a}$ is hydrogen, alkyl, haloalkyl, aryl, aralkyl, alkenyl, aralkenyl, cycloalkyl, heteroalkyl, heteroaryl or ester functional group;

$R^{2b}$ is alkyl, cycloalkyl, aralkyl, alkenyl, aralkenyl, heteroalkyl, or heteroaryl; and Z is a conjugated electron withdrawing group.

12. The method of claim 11, wherein TDP-43 expression is not affected.

* * * * *

UNITED STATES PATENT AND TRADEMARK OFFICE

CERTIFICATE OF CORRECTION

PATENT NO. : 11,147,795 B2
APPLICATION NO. : 16/515743
DATED : October 19, 2021
INVENTOR(S) : Jon T. Njardarson et al.

It is certified that error appears in the above-identified patent and that said Letters Patent is hereby corrected as shown below:

On the Title Page

Item (72), Inventors should read as follows:
Jon T. Njardarson, Tucson, AZ (US);
Isaac Chogii, Tucson, AZ (US);
David Townsend Smith, Tucson, AZ (US);
Edon Vitaku, Tucson, AZ (US);
Daniela C. Zarnescu, Tucson, AZ (US);
Rachel Ann Allen, Tucson, AZ (US)

Signed and Sealed this
Twenty-first Day of October, 2025

John A. Squires
*Director of the United States Patent and Trademark Office*